(12) United States Patent
Chen et al.

(10) Patent No.: US 12,193,703 B2
(45) Date of Patent: Jan. 14, 2025

(54) CUTTING INSTRUMENT WITH ASYMMETRIC BLADE

(71) Applicant: Pacesetter, Inc., Sylmar, CA (US)

(72) Inventors: Xiangqun Chen, Santa Clarita, CA (US); Rodney Hawkins, Santa Clarita, CA (US); Adam Evard, Los Angeles, CA (US); Alex Soriano, Ventura, CA (US); Ofer Rosenzweig, West Hills, CA (US)

(73) Assignee: Pacesetter, Inc., Sylmar, CA (US)

( * ) Notice: Subject to any disclaimer, the term of this patent is extended or adjusted under 35 U.S.C. 154(b) by 49 days.

(21) Appl. No.: 17/351,427

(22) Filed: Jun. 18, 2021

(65) Prior Publication Data

US 2022/0087708 A1    Mar. 24, 2022

Related U.S. Application Data

(60) Provisional application No. 63/082,109, filed on Sep. 23, 2020.

(51) Int. Cl.
| | | |
|---|---|---|
| A61B 17/3209 | (2006.01) | |
| A61B 17/32 | (2006.01) | |
| A61B 17/3211 | (2006.01) | |
| A61B 17/34 | (2006.01) | |
| A61F 9/007 | (2006.01) | |
| A61F 9/013 | (2006.01) | |
| B26B 21/56 | (2006.01) | |
| B26D 1/00 | (2006.01) | |

(52) U.S. Cl.
CPC ........ *A61B 17/32093* (2013.01); *A61B 17/32* (2013.01); *A61B 17/3209* (2013.01); *A61B 17/3211* (2013.01); *A61B 2017/3454* (2013.01); *A61F 9/007* (2013.01); *A61F 9/00754* (2013.01); *A61F 9/00763* (2013.01); *A61F 9/0133* (2013.01); *B26B 21/56* (2013.01); *B26D 2001/0053* (2013.01)

(58) Field of Classification Search
CPC .......... A61B 17/32093; A61B 17/3211; A61B 2017/3454; A61B 17/32; A61B 17/3209; A61F 9/0133; A61F 9/007; A61F 9/00763; A61F 9/00754; B26D 2001/0053; B26B 21/56
USPC .............................. 30/356, 357, 353, 346.57
See application file for complete search history.

(56) References Cited

U.S. PATENT DOCUMENTS

| | | | | |
|---|---|---|---|---|
| 1,194,044 | A * | 8/1916 | Loomis | ..................... B26B 9/00 |
| | | | | D7/693 |
| 1,472,378 | A * | 10/1923 | Wescott | ................... A22B 5/04 |
| | | | | 30/353 |
| 1,509,927 | A * | 9/1924 | Bowers | ..................... B67B 7/30 |
| | | | | 30/449 |

(Continued)

*Primary Examiner* — Brooke Labranche
*Assistant Examiner* — Mitchell Brian Hoag
(74) *Attorney, Agent, or Firm* — Dean D. Small; The Small Patent Law Group, LLC

(57) ABSTRACT

A blade for a cutting instrument includes a handle, a body, and at least three cutting edges along the body. The body has first and second sides extending along a longitudinal center axis. The body has a proximal end at the handle and a distal tip remote from the handle. The at least three cutting edges are oriented at corresponding angles with respect to the longitudinal center axis and are asymmetrically distributed with respect to the longitudinal center axis.

20 Claims, 4 Drawing Sheets

(56) References Cited

U.S. PATENT DOCUMENTS

| | | | | |
|---|---|---|---|---|
| 1,608,482 A * | 11/1926 | Cox | A47J 17/02 | 30/356 |
| 2,649,860 A * | 8/1953 | Royer | A61B 17/3211 | 30/353 |
| 2,753,632 A * | 7/1956 | Varn | A01D 1/06 | 30/356 |
| 4,712,546 A * | 12/1987 | Noe | A61B 17/32 | 433/144 |
| 4,944,647 A * | 7/1990 | Oleson | B67B 7/38 | 414/412 |
| 5,077,901 A * | 1/1992 | Warner | B23P 15/40 | 30/357 |
| 5,201,747 A * | 4/1993 | Mastel | A61B 17/3211 | 606/166 |
| 5,217,476 A * | 6/1993 | Wishinsky | A61F 9/0133 | 606/107 |
| 5,222,967 A * | 6/1993 | Casebeer | A61B 17/3211 | 606/166 |
| 5,258,002 A * | 11/1993 | Jeffers | A61B 17/3211 | 30/348 |
| 5,352,233 A * | 10/1994 | Anis | A61B 17/3211 | 606/166 |
| 5,370,652 A * | 12/1994 | Kellan | A61F 9/0133 | 30/294 |
| 6,099,543 A * | 8/2000 | Smith | A61F 9/0133 | 606/167 |
| 7,140,113 B2 * | 11/2006 | King | B26B 21/58 | 30/346.54 |
| 7,444,911 B2 * | 11/2008 | Sanda | B26D 1/245 | 83/425.2 |
| 2005/0028389 A1 * | 2/2005 | Wort | B26B 21/58 | 30/346.54 |
| 2005/0033335 A1 * | 2/2005 | Booth | A61B 17/3211 | 606/167 |
| 2006/0030788 A1 * | 2/2006 | Wong | A61B 5/150503 | 600/583 |
| 2006/0277767 A1 * | 12/2006 | Sun | B26B 21/60 | 30/346.54 |
| 2008/0250656 A1 * | 10/2008 | Lewis | B23P 15/28 | 30/356 |
| 2008/0319467 A1 * | 12/2008 | Wenchell | A61B 17/3496 | 606/170 |
| 2019/0159935 A1 * | 5/2019 | Klopotek | A61F 9/0133 | |
| 2020/0138514 A1 * | 5/2020 | Blumenkranz | A61B 18/1815 | |
| 2021/0100637 A1 * | 4/2021 | Yoon | A61C 3/025 | |

* cited by examiner

CUTTING INSTRUMENT WITH ASYMMETRIC BLADE

CROSS-REFERENCE TO RELATED APPLICATIONS

This application claims priority benefit to U.S. Provisional Application No. 63/082,109, which was filed on 23 Sep. 2020, and the entire disclosure of which is incorporated herein by reference.

BACKGROUND

Embodiments of the present disclosure relate generally to cutting instruments, and more particularly to handheld medical cutting instruments for skin puncture applications.

When making puncture incisions in a patient to implant a device, such as an implantable medical device (IMD), it is important to accurately control the width and depth of penetration to reduce the risk of injury to the patient. For example, deep cuts into the tissue could risk damaging blood vessels, tendons, bone, and/or the like. Controlling the width of the cut ensures that the incision is wide enough to insert the device. Conventional cutting instruments for these puncture-type applications have a symmetric, V-shaped blade. The symmetric V-shape enables control of the width and depth of penetration, but the drawback of this design is a relatively high required cutting force to penetrate the skin. The patient may experience discomfort if high forces are applied when making an incision. Furthermore, due to the high forces, the operator making the incision may have difficulty initiating the cut and/or finishing the cut at the desired width.

FIG. 1 depicts a graph 10 plotting the peak cutting force 12 required for four different conventional V-shaped blades. The different blades have different tip angles, which represents the angle between the two cutting surfaces at the tip of the blade (e.g., at the vertex or intersection of the "V"). The four represented blades includes a first blade 14 with a 120 degree tip angle, a second blade 16 with a 100 degree tip angle, a third blade 18 with an 80 degree tip angle, and a fourth blade 20 with a 60 degree tip angle. All four blades are symmetric about a longitudinal center axis, and all four have the same width 22. The graph indicates the tip angle of the blade substantially affects the cutting force for a given blade width. For example, the larger the tip angle, the higher the cutting force required to make the puncture incision. Based on the data in FIG. 1, for clinical applications that require skin puncture with a desired width, a V-shaped blade with a small tip angle, such as 60 degrees, is preferred to limit the manual cutting force. However, as shown in the depictions of the four blades in FIG. 1, smaller (e.g., more acute) tip angles necessitate longer length 24 blades for the given blade width. Longer blades provide deeper cuts, which can undesirably harm the patient as described above.

Accordingly, a need remains for a cutting instrument for providing skin punctures that achieves a desired skin opening width with limited manual cutting force and limited puncture depth.

SUMMARY

In an embodiment, a blade for a cutting instrument is provided that includes a handle, a body, and at least three cutting edges along the body. The body has first and second sides extending along a longitudinal center axis. The body has a proximal end at the handle and a distal tip remote from the handle. The at least three cutting edges are oriented at corresponding angles with respect to the longitudinal center axis and are asymmetrically distributed with respect to the longitudinal center axis.

The at least three cutting edges include first, second, and third cutting edges. The first and third cutting edges may be oriented at a common first angle with respect to the longitudinal center axis. The second cutting edge may be oriented at a different second angle with respect to the longitudinal center axis. The second angle may be greater than the first angle. The first angle may be no less than 20 degrees and no greater than 40 degrees, and the second angle may be no less than 45 degrees and no greater than 80 degrees. Optionally, the first and third cutting edges are located laterally from the longitudinal center axis. The second cutting edge may extend from a distal point of the third cutting edge to the distal tip of the body.

Optionally, the distal tip is laterally offset from the longitudinal center axis. Optionally, the distal tip is aligned with the longitudinal center axis. Optionally, each of the corresponding angles of the at least three cutting edges is no greater than 80 degrees with respect to the longitudinal center axis. Optionally, each of the at least three cutting edges is linear.

In an embodiment, a blade for a cutting instrument is provided that includes a handle, a body, opposite first and second non-cutting edges along the body, and at first, second, and third cutting edges along the body. The body has first and second sides extending along a longitudinal center axis. The body has a proximal end at the handle and a distal tip remote from the handle. The first and second non-cutting edges extend from the proximal end between the first and second sides, and are oriented parallel to the longitudinal center axis. The at least first, second, and third cutting edges are oriented at corresponding angles with respect to the longitudinal center axis. The first cutting edge extends from the first non-cutting edge, the third cutting edge extends from the second non-cutting edge, and the at least first, second, and third cutting edges are asymmetrically distributed with respect to the longitudinal center axis.

Optionally, the first and third cutting edges are oriented at a common first angle with respect to the longitudinal center axis. The second cutting edge may be oriented at a different second angle with respect to the longitudinal center axis. The second angle may be greater than the first angle.

The first, second, and third cutting edges are oriented at respective first, second, and third angles relative to the longitudinal center axis. Optionally, the first and third angles are each independently no less than 20 degrees and no greater than 40 degrees, and the second angle is no less than 45 degrees and no greater than 80 degrees. Optionally, the first, second, and third cutting edges and the first and second non-cutting edges are linear.

Optionally, the first and third cutting edges are laterally spaced apart from the longitudinal center axis, and the second cutting edge extends from a distal point of the third cutting edge to the distal tip of the body. The second cutting edge may intersect the longitudinal center axis, and the distal tip of the body may be laterally offset from the longitudinal center axis. Optionally, the distal tip of the body is aligned with the longitudinal center axis.

In an embodiment, a blade for a cutting instrument is provided that includes a handle, a body, and at least first, second, and third cutting edges along the body. The body has first and second sides extending along a longitudinal center axis. The body has a proximal end at the handle and a distal tip remote from the handle. The at least first, second, and third cutting edges are asymmetrically distributed with respect to the longitudinal center axis. The second cutting edge is disposed between the first and third cutting edges. The first, second, and third cutting edges are oriented at respective first, second, and third angles relative to the longitudinal center axis. The first and third angles are each independently no less than 20 degrees and no greater than 40 degrees, and the second angle is no less than 45 degrees and no greater than 80 degrees.

DETAILED DESCRIPTION

Embodiments set forth herein include handheld medical cutting instruments. The cutting instruments described herein are applicable to providing puncture-type incisions in the skin of a patient in which the blade of the instrument is inserted into the skin in a direction approximately perpendicular to the surface of the skin, and the width of the incision is controlled by the width of the blade. For example, unlike a scalpel, the blade may not be designed for dragging the cutting instrument along a length of the patient to create an elongated incision opening. the width of the blade may be selected based on the size of the incision opening that is required, such as to enable an implantable or insertable device, such as a catheter, an IMD (e.g., pacemaker and/or defibrillator), a dilator, and/or the like to enter the incision.

Figure 1:
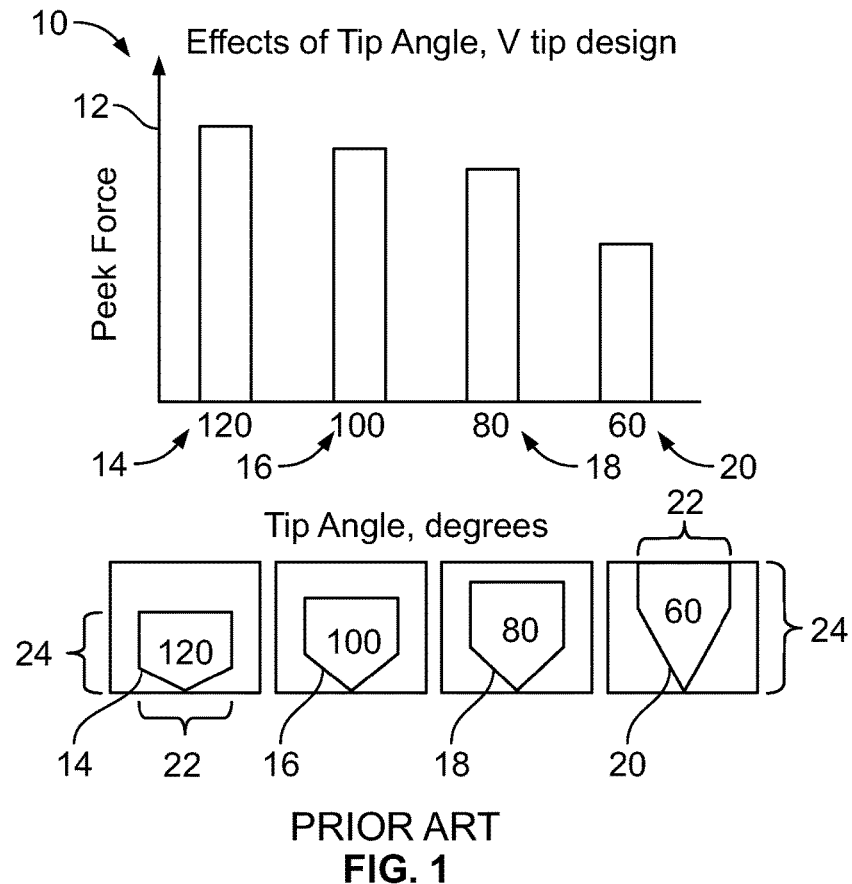
FIG. 1 is a graph depicting the peak cutting force of multiple symmetric, V-shaped blades with different tip angles.

Relative to known cutting devices, the blade of the cutting instrument according to the embodiments described herein has relatively low cutting force required to penetrate the skin of the patient and a relatively short length, which reduces the risk of injury to blood vessels, bone, and other tissue caused by excessive cutting depth. For example, with reference to the graph 10 in FIG. 1, the blade of the cutting instrument described herein may provide a peak cutting force that is similar to the peak cutting force of the 60-degree V-shaped blade 20 with a shorter length than the blade 20. The cutting instrument described herein may achieve shallower cuts than the blade 20 without requiring significantly more cutting force than the blade 20, for an overall improvement in performance and accuracy, and a reduced risk of injury to the patient.

The features, structures, or characteristics described herein may be combined in any suitable manner in one or more embodiments. In this description, numerous specific details are provided to give a thorough understanding of embodiments. One skilled in the relevant art will recognize, however, that the various embodiments can be practiced without one or more of the specific details, or with other methods, components, materials, etc. In other instances, well-known structures, materials, or operations are not shown or described in detail to avoid obfuscation. The description is intended only by way of example, and simply illustrates certain example embodiments.

Figure 2:
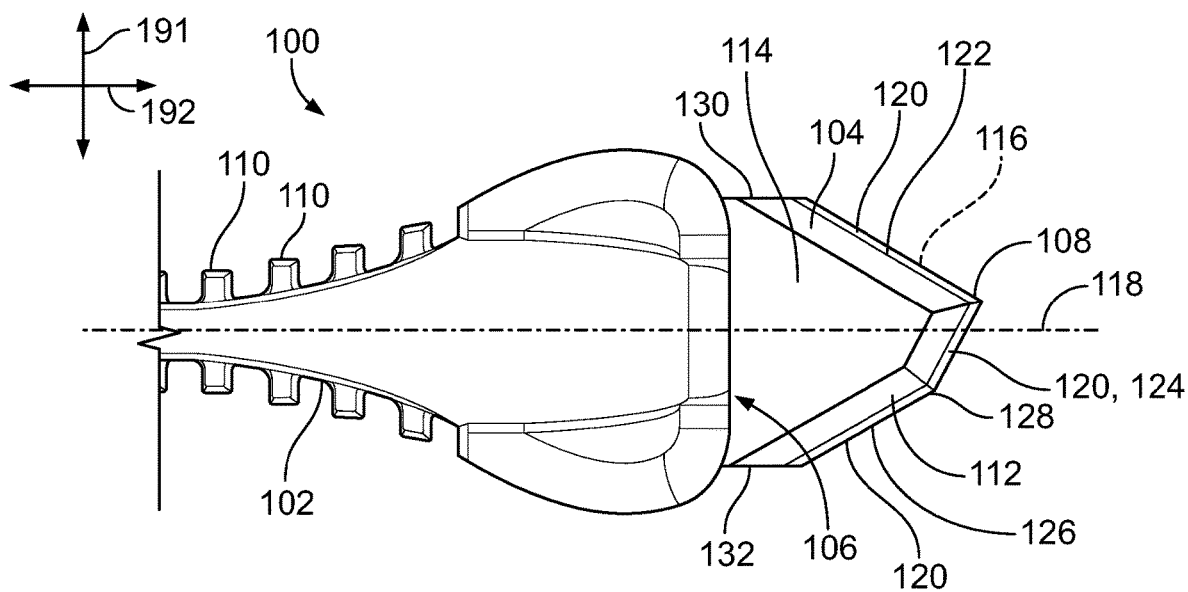
FIG. 2 illustrates a top-down view of a cutting instrument in accordance with an embodiment.

FIG. 2 illustrates a top-down view of a cutting instrument 100 in accordance with an embodiment. The cutting instrument 100 includes a handle 102 and a blade 104. The blade 104 is coupled or attached to the handle 102 and projects from the handle 102. For example, the blade 104 has a proximal end 106 at the handle 102 and extends from the proximal end 106 to a distal tip 108 of the blade 104 that is remote from the handle 102. The distal tip 108 represents the point of the blade 104 farthest from the handle 102. The cutting instrument 100 is arranged with respect to a width dimension 191 and a length dimension 192 that is perpendicular to the width dimension 191.

The handle 102 is an elongated shaft that is designed to be grasped and held by the hand of an operator, such as a medical doctor or other medical professional. A portion of the handle 102 is omitted in FIG. 2. The handle 102 may be composed of a rigid material, such as a thermoplastic or the like. In an embodiment, the material of the handle 102 may be molded (e.g., overmolded) onto the blade 104 to secure the blade 104 to the handle 102. The handle 102 optionally includes rib-like protrusions 110 or other small features to enhance the grip of the operator on the handle 102.

The blade 104 has a body 112. The body 112 may be formed of a metal material, such as steel (e.g., stainless, high carbon, tempered, etc.) or another metal or metal alloy. The body 112 has a first side 114 and a second side 116 extending along a longitudinal center axis 118. Only the first side 114 is shown in FIG. 2. The second side 116 is opposite the first side 114 and is the same as (or at least similar to) the first side 114 with respect to size, shape, and appearance. The first and second sides 114, 116 are planar in the illustrated embodiment, but may have a curvature in another embodiment. The longitudinal center axis 118 extends along the length dimension 192 and bisects the cutting instrument 100 along the width dimension 191. For example, half of the width of the blade 104 is disposed on one side of the longitudinal center axis 118, and the other half of the blade 104 is disposed on the other side of the longitudinal center axis 118.

The body 112 of the blade 104 has at least three cutting edges 120 between the first and second sides 114, 116. The cutting edges 120 are sharpened, such as honed or whetted, for slicing through tissue with limited resistance. The body 112 may taper from the first and second sides 114, 116 along the cutting edges 120 to provide the sharpened edges. In one or more embodiments, the cutting edges 120 are oriented at corresponding angles with respect to the longitudinal center axis 118. For example, each of the corresponding angles may be less than 90 degrees, such that all cutting edges 120 are transverse to the longitudinal center axis 118. In a non-limiting example, each of the corresponding angles may be no greater than (e.g., less than or equal to) 80 degrees relative to the longitudinal center axis 118, and more particularly may be no greater than 70 degrees relative to the axis 118. The cutting edges 120 are asymmetrically distributed with respect to the longitudinal center axis 118. The cutting edges 120 are asymmetrically distributed such that the blade 104 is not symmetric about the longitudinal center axis 118. For example, the half of blade 104 above the longitudinal center axis 118 in FIG. 2 is not a mirror image of the half of the blade 104 below the longitudinal center axis 118.

Figure 7:
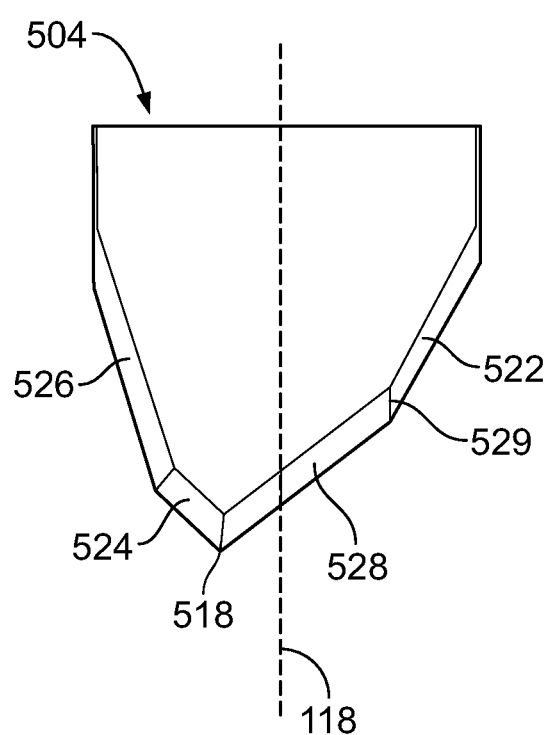
FIG. 7 is a top-down view of a blade of the cutting instrument in accordance with a third embodiment.

In the illustrated embodiment, the body 112 of the blade 104 has three cutting edges 120. The three cutting edges 120 include a first cutting edge 122, a second cutting edge 124, and a third cutting edge 126. The second cutting edge 124 is disposed between the first and third cutting edges 122, 126. For example, the second cutting edge 124 extends from a distal point 128 of the third cutting edge 126 to the distal tip 108 of the body 112. The distal tip 108 is defined by the vertex or intersection between the first cutting edge 122 and the second cutting edge 124. The three cutting edges 122, 124, 126, are linear in the illustrated embodiment. The first and third cutting edges 122, 126 are located laterally from the longitudinal center axis 118, such that the edges 122, 126 are spaced apart from the axis 118 and do not intersect the axis 118. The second cutting edge 124 intersects the longitudinal center axis 118 in the illustrated embodiment, and the distal tip 108 of the body 112 is laterally offset from the longitudinal center axis 118. The distal tip 108 may align with the longitudinal center axis 118 in another embodiment, while retaining the asymmetry of the body 112, as shown in FIG. 7. Furthermore, the body 112 of the blade 104 may have more than three cutting edges 120 in another embodiment, such as four, five, six, or the like. For example, at least one additional cutting edge may be disposed between the second cutting edge 124 and the first cutting edge 122 and/or between the second cutting edge 124 and the third cutting edge 126.

The body 112 also includes a first non-cutting edge 130 and a second non-cutting edge 132. The non-cutting edges 130, 132 are disposed between the first and second sides 114, 116 of the body 112. The first non-cutting edge 130 is located opposite the second non-cutting edge 132, and the distance therebetween represents the define the width of the blade 104. The non-cutting edges 130, 132 are not sharpened for slicing through tissue, unlike the cutting edges 120. As such, the non-cutting edges 130, 132 may be relatively dull and/or blunt. The non-cutting edges 130, 132 extend from the handle 102 at the proximal end 106 of the blade 104. The first cutting edge 122 extends from the first non-cutting edge 130. The third cutting edge 126 extends from the second non-cutting edge 132.

Figure 3:
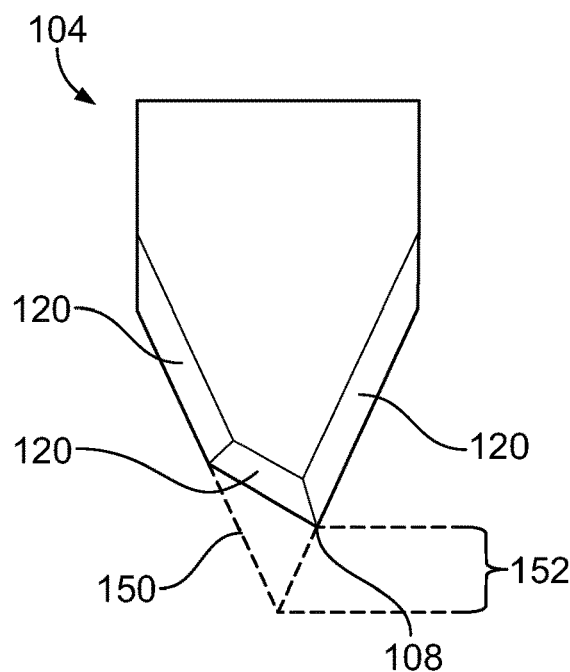
FIG. 3 is a top-down view of a blade of the cutting instrument shown in FIG. 2 with a handle of the cutting instrument omitted.

FIG. 3 is a top-down view of the blade 104 of the cutting instrument 100 shown in FIG. 2 with the handle 102 omitted. The blade 104 is rotated relative to the orientation shown in FIG. 2 such that the distal tip 108 points downward in FIG. 3. In FIG. 3, the blade 104 is superimposed over an outline 150 that represents a symmetric, V-shaped blade as known in the art. For example, the outline 150 could represent the 60-degree blade 20 shown in FIG. 1. Compared to the conventional symmetric, V-shaped blade 150, the blade 104 in accordance with the embodiments described herein has a shorter length by a significant margin 152. Furthermore, when compared to conventional symmetric, V-shaped blades that have a similar length, such as the 100 degree blade 14 in FIG. 1, the angle at the distal tip 108 is more acute than the blade 14, which reduces the peak cutting force by creating a steeper point to initiate the incision. The blade 104 advantageously reduces the blade length while maintaining characteristics of blades that have smaller (e.g., more acute) tip angles. For example, the more acute distal tip angle promotes lower initial puncture forces and the honed cutting edges 120 reduce the cutting force throughout the entire incision-generating process. This combination may provide the operator the ability to initiate the incision with less manual force applied than known blades of similar length, and to control the amount of pressure applied to accurately complete the incision to a desired width and depth.

Figure 4:
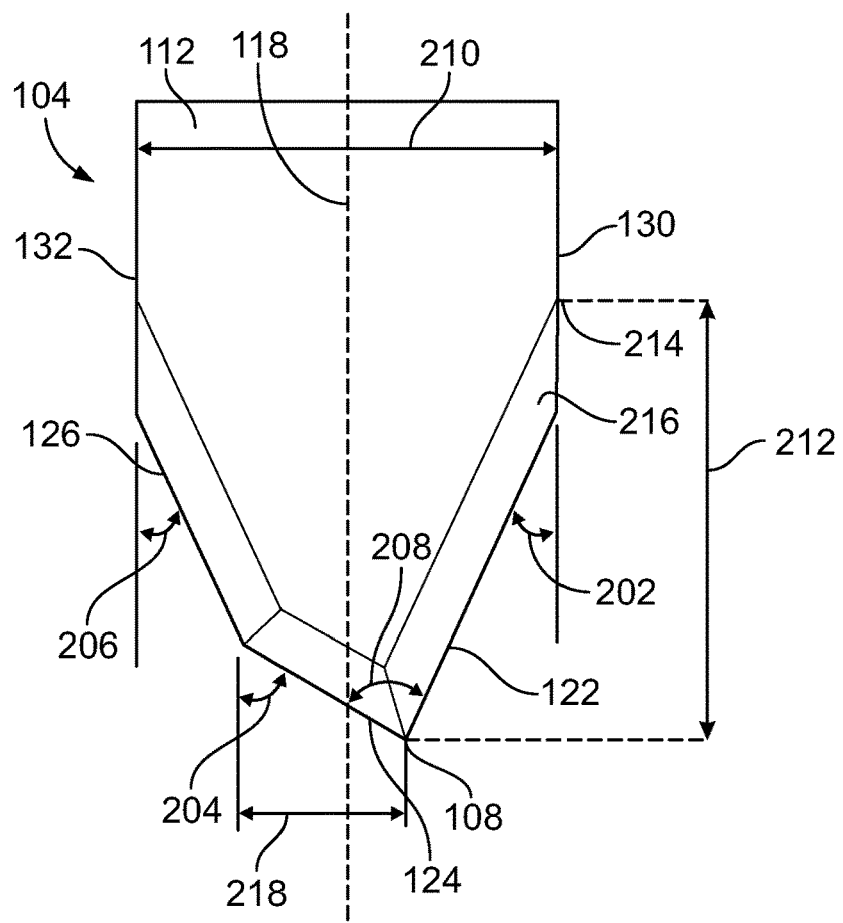
FIG. 4 is an enlarged top-down view of the blade of the cutting instrument shown in FIGS. 2 and 3.

FIG. 4 is an enlarged top-down view of the blade 104 of the cutting instrument 100 shown in FIGS. 2 and 3. The various edges of the blade 104 define corresponding angles relative to each other and to the longitudinal center axis 118. For example, the first and second non-cutting edges 130, 132 are both oriented parallel to the longitudinal center axis 118 in the illustrated embodiment. The first cutting edge 122 is oriented at a first angle 202 relative to the longitudinal center axis 118. The second cutting edge 124 is oriented at a second angle 204 relative to the longitudinal center axis 118. The third cutting edge 126 is oriented at a third angle 206 relative to the longitudinal center axis 118. Because the non-cutting edges 130, 132 are parallel to the longitudinal center axis 118, the first, second, and third cutting edges 122, 124, 126 are also oriented at the respective first, second, and third angles 202, 204, 206 relative to the first and second non-cutting edges 130, 132. The first, second, and third angles 202, 204, 206 are each less than 90 degrees, and may be no greater than 80 degrees.

In an embodiment, the first and third angles 202, 206 are each independently between 15 degrees and 45 degrees. As used herein, a range of angles is inclusive of the endpoints such that 15-45 degrees means no less than 15 degrees and no greater than 45 degrees. In a non-limiting example, the first and third angles 202, 206 are each independently between 20 degrees and 40 degrees. The first angle 202 optionally may be the same as the third angle 206, such that the first and third cutting edges 122, 126 are oriented at a common first angle with respect to the longitudinal center axis 118. For example, the first and third angles 202, 206 may be 30 degrees in the illustrated embodiment. In an alternative embodiment, the first angle 202 is different from the third angle 206.

The second angle 204 defined between the second cutting edge 124 and the longitudinal center axis 118 is different from the first and third angle 202, 206. The second angle 204 may be greater than the first and third angles 202, 206, and may be between 45 degrees and 80 degrees. In a non-limiting example, the second angle 204 is between 50 degrees and 70 degrees. The second angle 204 may be 60 degrees in the illustrated embodiment. In the illustrated embodiment in which the first and third angles 202, 206 are 30 degrees and the second angle 204 is 60 degrees, the blade tip angle 208, defined between the first cutting edge 122 and the second cutting edge 124, is 90 degrees. The first, second and third angles 202, 206 and 208 define an asymmetrical distribution for the first, second and third cutting edges 122, 124, 126 with respect to the longitudinal center axis 118.

As shown, the blade tip 108 is offset from the longitudinal center axis 118. In other embodiments, the blade tip angle 208 may be greater or less than 90 degrees, such as between 80 degrees and 100 degrees.

The width 210 of the blade 104 is the distance between the first and second non-cutting edges 130, 132. The length 212 of a cutting portion of the blade 104 is the distance from the distal tip 108 to the proximal end 214 of the honed or tapered surfaces 216 of the body 112. In an embodiment, the lengths and orientations of the cutting edges 122, 124, 126 may be designed based on total width 210 and/or length 212 constraints. One constraint may designate that a width 218 of the second cutting surface 124 (parallel to the width dimension 191 shown in FIG. 2) is within a designated range of the overall width 210 of the blade 104. For example, the width 218 of the second cutting surface 124 may be between 15% and 50% of the blade width 210 (inclusive of the end points). In the illustrated embodiment, the width 218 is 37%-40% of the blade width 210.

Figure 5:
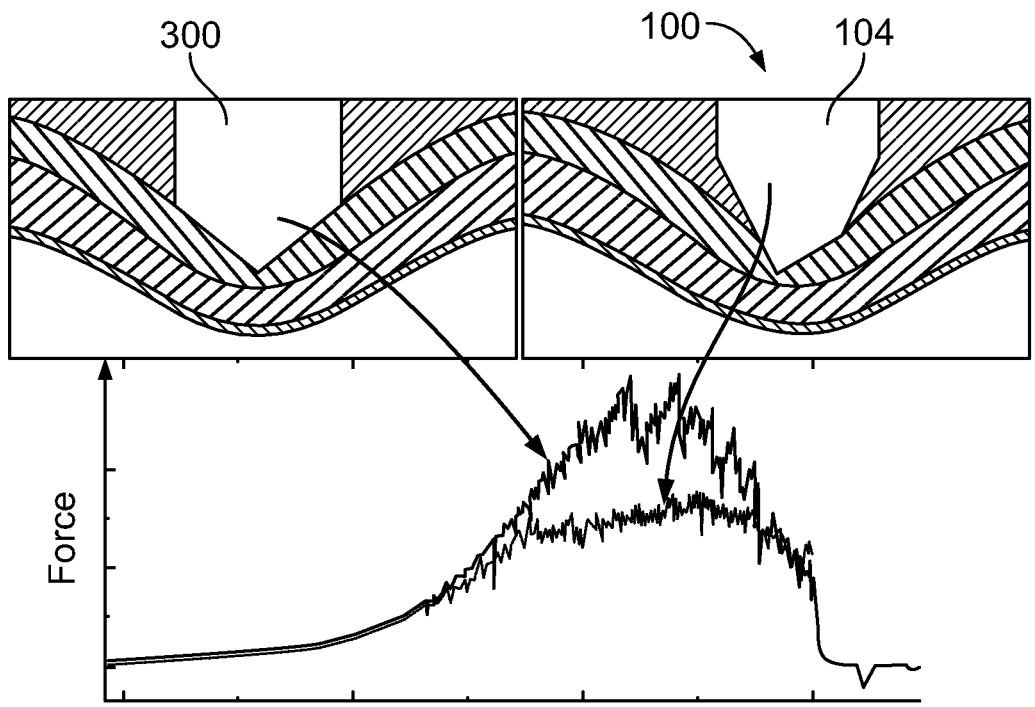
FIG. 5 is a diagram comparing the cutting forces between the cutting instrument shown in FIGS. 2-4 and a conventional symmetric, V-shaped blade.

The cutting instrument 100 according to the embodiments of the present disclosure has been experimentally tested to compare the cutting instrument 100 to conventional blade types, including the symmetric, V-shaped blades. FIG. 5 is a diagram comparing the cutting forces between the cutting instrument 100 described herein and a conventional V-shaped blade 300. The V-shaped blade 300 used as the reference in the evaluation has a 100 degree tip angle, similar to the blade 16 in FIG. 1. Bench testing was performed in which the blades 104, 300 were punctured vertically into a synthetic muscular skin tissue plate with the tissue mounted and backed by a foam block. The asymmetric blade 104 of the cutting instrument 100 achieves lower cutting force than the reference blade 300 while maintaining a desirable short blade length to avoid deep cuts that could unintentionally sever blood vessels, scrape bone, or the like.

Figure 6:
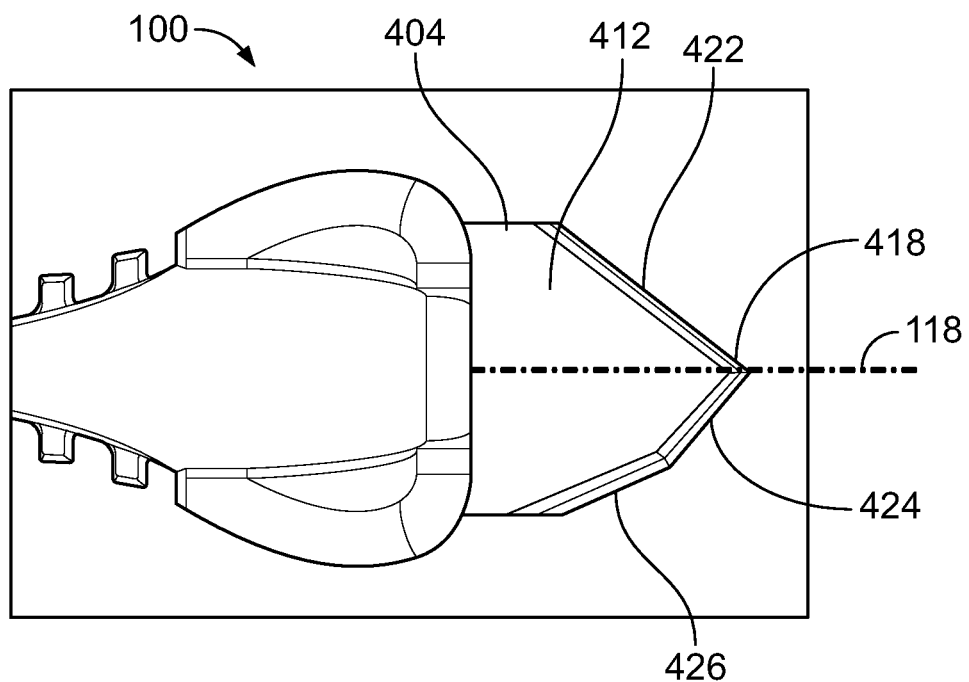
FIG. 6 illustrates a top-down view of the cutting instrument in accordance with a second embodiment.

FIG. 6 illustrates a top-down view of the cutting instrument 100 in accordance with a second embodiment. The cutting instrument 100 has a blade 404 that is similar to the blade 104 shown in FIGS. 2-5. For example, the blade 404 has a body 412 with a first cutting edge 422, a second cutting edge 424, and a third cutting edge 426 that are oriented at corresponding angles with respect to the longitudinal center axis 118, and the cutting edges 422, 424, 426 are asymmetrically distributed with respect to the longitudinal center axis 118. The angles define the asymmetrical distribution for the first, second and third cutting edges 422, 424, 426 with respect to the longitudinal center axis 118. However, unlike the blade 104, a distal tip 418 of the blade 404, which is at the vertex or intersection between the first and second cutting edges 422, 424, aligns with the longitudinal center axis 118. In the illustrated embodiment, the blade 404 is asymmetric about the longitudinal center axis 118, even though the distal tip 418 aligns with the axis 118, because the upper half of the blade 404 above the axis 118 in FIG. 6 is not a mirror image of the lower half of the blade 404 below the axis 118. For example, the upper half of the blade 404 resembles the symmetric V-shaped blades, but the lower half does not. There is only one cutting edge 422 above the axis 118, and two cutting edges 424, 426 below the axis 118. Experimental testing has demonstrated similar performance between the two embodiments of the asymmetric blades 104, 404. The blade 404 with the centered blade tip 418 required only slightly higher total puncture (or cutting) force than the blade 104 with the offset blade tip 108.

FIG. 7 is a top-down view of a blade 504 of the cutting instrument 100 in accordance with a third embodiment. The blade 504 is similar to the blade 104 shown in FIGS. 2 through 5. For example, the blade 504 has a distal tip 518 that is offset from the longitudinal center axis 118 of the blade 504. The blade 504 differs from the blade 104 and the blade 404 shown in FIG. 6 because the blade 504 has four cutting edges, including a first cutting edge 522, a second cutting edge 524, a third cutting edge 526, and a fourth cutting edge 528. The first and third cutting edges 522, 526 extend from different non-cutting edges of the blade 504. The fourth cutting edge 528 extends from a distal point 529 of the first cutting edge 522 to the distal tip 518. The second cutting edge 524 extends from a distal point of the third cutting edge 526 to the distal tip 518. The distal tip 518 is defined at the vertex or intersection between the second and fourth cutting edges 524, 528. The cutting edges 522, 524, 526, 528 are linear, honed edges. In the illustrated embodiment, the first, second, and third cutting edges 522, 524, 526 are laterally spaced apart from the longitudinal center axis 118, and the fourth cutting edge 528 intersects the longitudinal center axis 118. The cutting edges 522, 524, 526, 528 are asymmetrically distributed with respect to the longitudinal center axis 118.

Each of the cutting edges 522, 524, 526, 528 is oriented transverse to the longitudinal center axis 118, such that the corresponding angle between the respective cutting edge and the axis 118 is less than 90 degrees. For example, the first, second, third, and fourth cutting edges 522, 524, 526, 528 are oriented at respective first, second, third, and fourth angles relative to the longitudinal center axis 118. The first and third angles may be each independently no less than 20 degrees and no greater than 40 degrees, and the second and fourth angles may be no less than 45 degrees and no greater than 80 degrees (such as no less than 50 degrees and no greater than 70 degrees). The first and third angles may be the same or different from each other. The second and fourth angles may be the same or different from each other.

The cutting instrument with asymmetric blade as described herein advantageously enables accurate control over the width and depth of puncture-type incisions while reducing the amount of force that is required to be exerted on the cutting instrument relative to cutting instruments with blades of comparable length. The blade of the cutting instrument described herein is a hybrid design that provides the both the penetration benefit of a longer, narrow tip angle V-shaped blade and the shallow depth control of a wider tip angle V-shaped blade, while avoiding or reducing the shortcomings of these two V-shaped blades.

It will be readily understood that the components of the embodiments as generally described and illustrated in the Figures herein, may be arranged and designed in a wide variety of different configurations in addition to the described example embodiments. Thus, the more detailed description of the example embodiments, as represented in the Figures, is not intended to limit the scope of the embodiments, as claimed, but is merely representative of example embodiments.

Reference throughout this specification to "one embodiment" or "an embodiment" (or the like) means that a particular feature, structure, or characteristic described in connection with the embodiment is included in at least one embodiment. Thus, appearances of the phrases "in one embodiment" or "in an embodiment" or the like in various places throughout this specification are not necessarily all referring to the same embodiment.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the inventive subject matter without departing from its scope. While the dimensions and types of materials described herein are intended to define the parameters of the inventive subject matter, they are by no means limiting and are exemplary embodiments. Many other embodiments will be apparent to one of ordinary skill in the art upon reviewing the above description. The scope of the inventive subject matter should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. § 112(f) unless and until such claim limitations expressly use the phrase "means for" followed by a statement of function void of further structure.

What is claimed is:

1. A medical cutting instrument, comprising:
a blade having a body extending along a longitudinal center axis, the body having a proximal end configured to attach to a handle and a distal tip remote from the handle,
first, second, and third cutting edges along the body oriented at corresponding angles with respect to the longitudinal center axis, each of the corresponding angles being non-zero and less than 90 degrees, the first, second, and third cutting edges asymmetrically distributed with respect to the longitudinal center axis to initiate a puncture-type incision in patient tissue with a desired puncture force, wherein the second cutting edge extends from the first cutting edge to the third cutting edge and intersects the longitudinal center axis,
wherein the body includes opposite first and second non-cutting edges that define a width of the blade to limit a width of the puncture-type incision, wherein the first cutting edge extends from the first non-cutting edge and the third cutting edge extends from the second non-cutting edge.

2. The medical cutting instrument of claim 1, wherein the first and third cutting edges are oriented at a common first angle with respect to the longitudinal center axis, the second cutting edge is oriented at a second angle with respect to the longitudinal center axis, and the second angle is different from the first angle.

3. The medical cutting instrument of claim 2, wherein the first angle is no less than 20 degrees and no greater than 40 degrees, and the second angle is no less than 45 degrees and no greater than 80 degrees.

4. The medical cutting instrument of claim 1, wherein the first and second non-cutting edges are linear and extend parallel to the longitudinal axis.

5. The medical cutting instrument of claim 1, wherein each of the corresponding angles of the first, second, and third cutting edges is no greater than 80 degrees with respect to the longitudinal center axis.

6. The medical cutting instrument of claim 1, wherein each of the first, second, and third cutting edges is linear.

7. The medical cutting instrument of claim 1, wherein the distal tip is at an intersection between the first and second cutting edges.

8. The medical cutting instrument of claim 7, wherein the distal tip is laterally offset from the longitudinal center axis.

9. The medical cutting instrument of claim 7, wherein the distal tip is aligned with the longitudinal center axis.

10. The medical cutting instrument of claim 1, wherein the blade is asymmetric about the longitudinal center axis.

11. The medical cutting instrument of claim 1, wherein each of the first, second, and third cutting edges extends a thickness of the blade from a top surface of the blade to a bottom surface of the blade that is opposite the top surface, the top surface and the bottom surface extending a length of the blade and a width of the blade, wherein the length and width of the blade are each greater than the thickness of the blade.

12. The medical cutting instrument of claim 1, wherein each of the first, second, and third cutting edges is sharpened to taper to a respective sharp point for slicing through tissue of the patient at the puncture-type incision.

13. A medical cutting instrument, comprising:
a blade having a body extending along a longitudinal center axis, the body having a proximal end configured to attach to a handle and a distal tip remote from the handle,
wherein the blade has opposite first and second non-cutting edges that are linear, extend parallel to the longitudinal center axis, and define a width of the blade,
wherein the blade includes first, second, and third cutting edges along the body that are linear and are oriented at corresponding angles with respect to the longitudinal center axis, each of the corresponding angles being non-zero and less than 90 degrees,
wherein the first cutting edge extends from the first non-cutting edge, the third cutting edge extends from the second non-cutting edge, and the first and third cutting edges are laterally spaced apart from the longitudinal center axis, wherein the second cutting edge extends from the first cutting edge to the third cutting edge and intersects the longitudinal center axis, the distal tip defined at an intersection between the first cutting edge and the second cutting edge, and
wherein the first, second, and third cutting edges are asymmetrically distributed with respect to the longitudinal center axis to initiate a puncture-type incision in patient tissue with a desired puncture force and a width limited to the width of the blade.

14. The medical cutting instrument of claim 13, wherein the first and third cutting edges are oriented at a common first angle with respect to the longitudinal center axis, and the second cutting edge is oriented at a different second angle with respect to the longitudinal center axis.

15. The medical cutting instrument of claim 13, wherein the first, second, and third cutting edges are oriented at respective first, second, and third angles relative to the longitudinal center axis, wherein the first and third angles are each independently no less than 20 degrees and no greater than 40 degrees, and the second angle is no less than 45 degrees and no greater than 80 degrees.

16. The medical cutting instrument of claim 13, wherein the distal tip of the body is laterally offset from the longitudinal center axis.

17. The medical cutting instrument of claim 13, wherein the distal tip of the body is aligned with the longitudinal center axis.

18. A medical cutting instrument comprising:
a handle; and
a blade including a body extending along a longitudinal center axis from the handle to a distal tip of the body, the body including first, second, and third cutting edges asymmetrically distributed with respect to the longitudinal center axis to initiate a puncture-type incision in patient tissue with a desired puncture force,
wherein the second cutting edge is disposed between the first and third cutting edges and extends from the first cutting edge to the third cutting edge, wherein the distal tip is defined at an intersection between the first cutting edge and the second cutting edge, and the distal tip is aligned with the longitudinal center axis, and
wherein the first, second, and third cutting edges are oriented at respective first, second, and third angles relative to the longitudinal center axis, wherein the first and third angles are each independently no less than 20 degrees and no greater than 40 degrees, and the second angle is no less than 45 degrees and no greater than 80 degrees.

19. The medical cutting instrument of claim 18, wherein the blade has opposite first and second non-cutting edges that are linear, extend parallel to the longitudinal center axis, and define a width of the blade, wherein the first cutting edge extends from the first non-cutting edge and the third cutting edge extends from the second non-cutting edge.

20. The medical cutting instrument of claim 18, wherein each of the first, second, and third cutting edges is linear.

* * * * *